United States Patent
Yang

(10) Patent No.: US 10,265,360 B2
(45) Date of Patent: *Apr. 23, 2019

(54) FEED ADDITIVE FOR SWINE AND FEED COMPOSITION CONTAINING THE SAME

(71) Applicant: Shenzhen Seefaa Scitech Co., Ltd., Shenzhen (CN)

(72) Inventor: Chenglin Yang, Dongguan (CN)

(73) Assignee: Shenzhen Seefaa Scitech Co., Ltd., Shenzhen (CN)

( * ) Notice: Subject to any disclaimer, the term of this patent is extended or adjusted under 35 U.S.C. 154(b) by 348 days.

This patent is subject to a terminal disclaimer.

(21) Appl. No.: 15/003,900

(22) Filed: Jan. 22, 2016

(65) Prior Publication Data
US 2016/0143322 A1    May 26, 2016

Related U.S. Application Data

(63) Continuation-in-part of application No. PCT/CN2014/082020, filed on Jul. 11, 2014.

(30) Foreign Application Priority Data

Jul. 26, 2013   (WO) ................ PCT/CN2013/080189

(51) Int. Cl.
| | | |
|---|---|---|
| *A61K 36/00* | (2006.01) | |
| *A61K 36/34* | (2006.01) | |
| *A61K 36/35* | (2006.01) | |
| *A61K 36/31* | (2006.01) | |
| *A61K 36/48* | (2006.01) | |
| *A61K 36/33* | (2006.01) | |
| *A61K 36/185* | (2006.01) | |
| *A61K 36/19* | (2006.01) | |
| *A61K 36/233* | (2006.01) | |
| *A61K 36/28* | (2006.01) | |
| *A61K 36/315* | (2006.01) | |
| *A61K 36/344* | (2006.01) | |
| *A61K 36/725* | (2006.01) | |
| *A23K 1/14* | (2006.01) | |
| *A23K 1/18* | (2006.01) | |
| *A61K 31/718* | (2006.01) | |
| *A61K 36/287* | (2006.01) | |
| *A61K 36/355* | (2006.01) | |
| *A61K 31/185* | (2006.01) | |
| *A61K 36/481* | (2006.01) | |
| *A61K 36/484* | (2006.01) | |
| *A61K 36/8964* | (2006.01) | |

(52) U.S. Cl.
CPC .............. *A61K 36/185* (2013.01); *A23K 1/14* (2013.01); *A23K 1/184* (2013.01); *A61K 31/185* (2013.01); *A61K 31/718* (2013.01); *A61K 36/19* (2013.01); *A61K 36/233* (2013.01); *A61K 36/28* (2013.01); *A61K 36/287* (2013.01); *A61K 36/315* (2013.01); *A61K 36/33* (2013.01); *A61K 36/344* (2013.01); *A61K 36/35* (2013.01); *A61K 36/355* (2013.01); *A61K 36/481* (2013.01); *A61K 36/484* (2013.01); *A61K 36/725* (2013.01); *A61K 36/8964* (2013.01)

(58) Field of Classification Search
None
See application file for complete search history.

(56) References Cited

U.S. PATENT DOCUMENTS

| | | | | |
|---|---|---|---|---|
| 2009/0310839 A1* | 12/2009 | Katzenelson | .......... | C12Q 1/025 382/128 |
| 2012/0201909 A1* | 8/2012 | Sanabria | ................ | A61K 36/00 424/727 |
| 2015/0296851 A1* | 10/2015 | Zhao | ........................ | A23F 3/34 426/2 |

* cited by examiner

*Primary Examiner* — Christopher R Tate
*Assistant Examiner* — Randall Winston
(74) *Attorney, Agent, or Firm* — Hemisphere Law, PLLC

(57) ABSTRACT

A feed additive for swine consists of following ingredients measured by weight: 20-50 sour jujubes, 10-18 radix bupleuri, 6-20 *codonopsis pilosula*, 10-20 honeysuckles, 10-20 *isatis* roots, 3-6 *astragalus propinquus*, 10-20 *myrica rubra* and 30-60 cactuses. The disclosure further provides a feed composition for swine with the above feed additive. The above-mentioned feed additive for swine is effective in preventing hog cholera, convenient in use, no toxicity, side effects or medical residue, which benefits human health.

5 Claims, No Drawings

FEED ADDITIVE FOR SWINE AND FEED COMPOSITION CONTAINING THE SAME

BACKGROUND

1. Technical Field

The disclosure relates to a livestock feed, and more particularly to a feed additive for swine a feed composition containing the same.

2. Description of the Related Art

Swine breeding grows rapidly in recent years as a major emphasis of livestock breeding. Threats of various diseases of swine have long been barriers of development of swine breeding, especially hog cholera.

Hog cholera is an infectious viral disease that is characterized by acute infection, fever and being spread by contact. Before an infected pig shows clinical signs, the virus can be contagious by secretion from mouths, noses and eyes, as well as urine and feces. Swine are the only natural hosts of hog cholera, infected pigs and viral carriers are the main source of infection, and viruses are spread by direct contact of infected pigs and non-infected pigs. A conventional method of dealing with infected pigs is insulation. Some precious species can be treated by anti-swine-fever serum, but corresponding costs are high. Therefore, prevention and an immediate response are vital to control and eradicate hog cholera, which can reduce economic loss.

SUMMARY

It is necessary to provide a feed additive for swine a feed composition using the same according to the previous situation.

A feed additive for swine consists of following ingredients measured by weight: 20-50 sour jujubes, 10-18 radix bupleuri, 6-20 *codonopsis pilosula,* 10-20 honeysuckles, 10-20 *isatis* roots, 3-6*astragalus propinquus,* 10-20 *myrica rubra* and 30-60 cactuses.

A feed composition for swine includes a main feed and an additive, wherein the additive is processed by mixing, grinding, sifting following ingredients measured by weight: 20-50 sour jujubes, 10-18 radix bupleuri, 6-20 *codonopsis pilosula,* 10-20 honeysuckles, 10-20 *isatis* roots, 3-6 *astragalus propinquus,* 10-20 *myrica rubra* and 30-60 cactuses.

A process for feeding swine includes feeding the swine a feed composition to produce a finished, market-ready weight. The feed composition includes a main feed and an additive, wherein the additive is processed by mixing, grinding, sifting following ingredients measured by weight: 20-50 sour jujubes, 10-18 radix bupleuri, 6-20 *codonopsis pilosula,* 10-20 honeysuckles, 10-20 *isatis* roots, 3-6 *astragalus propinquus,* 10-20 *myrica rubra* and 30-60 cactuses.

The feed additive for swine above can be effective in preventing diseases (such as hog cholera), convenient in use, no toxicity, side effects or medical residue, which benefits human health.

DETAILED DESCRIPTION

With the following reference, concrete embodiments of the disclosure will be described in detail.

The disclosure aims at providing an additive that can improve immunity and disease resistance of swine to prevent diseases, such as an outbreak of hog cholera, the treatment is safe, nontoxic; side effects, resistance to drugs or medical residue in pork can be avoided.

A feed additive for swine consists of following ingredients measured by weight: 20-50 sour jujubes, 10-18 radix bupleuri, 6-20 *codonopsis pilosula,* 10-20 honeysuckles, 10-20 *isatis* roots, 3-6 *astragalus propinquus,* 10-20 *myrica rubra* and 30-60 cactuses.

Preferably, the feed additive for swine according to the exemplary embodiment of the disclosure consists of 35 sour jujubes, 16 radix bupleuri, 12 *codonopsis pilosula,* 15 honeysuckles, 15 *isatis* roots, 5 *astragalus propinquus,* 15 *myrica rubra* and 50 cactuses.

The previous feed additive for swine can be firstly immersed, ground and mixed, after being sifted by a sieve (such as a sieve with a mesh number 200), medical powders are prepared.

Pharmacological principles of the feed additive for swine according to the disclosure are as follows:

Sour jujubes can nourish livers, calm hearts and nerves, decrease perspiration and resist diseases; radix bupleuri has functions of defervescence and taking care of livers; *codonopsis pilosula* can supple energy, strengthen resistance to eliminate pathogenic factors, excite nerves, regulate gastrointestinal functions, enhance immunity and resistance to diseases, as well as promote growth; honeysuckles are not only antipyretic and antidotal, but also comforting throats and relieving diarrhea; *isatis* roots are both antipyretic and antidotal, resisting bacteria and viruses, comforting throats and improving immunity; *astragalus propinquus* can improve immunity, protect livers, diuresis, anti-ageing, anti-stress, reduce blood pressure and widely resist bacteria; *myrica rubra* can be antipyretic and antidotal, help produce saliva and quench thirst, empty guts and stomachs; cactuses can invigorate the circulation of blood, antipyretic and antidotal, invigorate the spleen to arrest diarrhea, calm nerves and diuresis.

Therefore, sour jujubes, *codonopsis pilosula, isatis* roots and *astragalus propinquus* are added in the feed additive for swine to invigorate spleen, strengthen resistance to eliminate pathogenic factors, improve immunity and resistance to diseases, viruses are prevented and hog cholera will not be spread; radix bupleuri, honeysuckles and cactuses are antipyretic and antidotal, eliminating dampness and diuresis, antitussive and antiasthmatic, antibacterial, diminishing inflammation, inhibiting viral replication and killing viruses; sour jujubes and *myrica rubra* are applied to promote digestion and blood circulation, which can improve immunity and disease resistance.

The feed additive for swine of the disclosure can prevent an outbreak of hog cholera. 6 feed additives for swine are added into 1000 main feeds and mixed thoroughly to feed swine, hog cholera can be prevented. The main feed of the feed for swine can contains at least one of an animal protein product, marine product, milk product, grain product, plant protein product and processed grain by-product.

The feed additive for swine of the disclosure is effective in preventing diseases (such as hog cholera), convenient in use, no toxicity, side effects or medical residue, which benefits human health.

An exemplary embodiment:

35 sour jujubes, 16 radix bupleuri, 12 *codonopsis pilosula,* 15 honeysuckles, 15 *isatis* roots, 5 *astragalus propinquus,* 15 *myrica rubra* and 50 cactuses are immersed, ground and mixed, after being sifted by a sieve (such as a sieve with a mesh number 200), medical powders are prepared. 0.6 kilograms feed additives for swine are added into 100 kilograms main feeds from the market and mixed thoroughly to feed swine, the rate of preventing hog cholera can be 95%.

To prove effects of the additive of the disclosure, 400 swine are divided into a control group and a trial group for testing. The control group are fed a conventional additive, the trial group are fed 0.6 kilograms feed additive for swine preventing hog cholera according to the disclosure added into 100 kilograms main feeds for preventing hog cholera. Rates of growth are referred as a criterion to judge efficiency, morbidity and mortality. Results are as shown, the control group: 200 swine are fed the conventional additive, 128 healthy swine, 72 infected swine, 16 dead swine, an effective rate is 64%, an infection rate is 36%, a mortality rate is 8%; the trial group: 200 swine are fed the feed additive for swine of the disclosure, 190 healthy swine, 10 infected swine, 4 dead swine, an effective rate is 95%, an infection rate is 5%, a mortality rate is 2%.

Results turn out the feed additive for swine of the disclosure is more efficient in preventing hog cholera than other additives.

The feed additive for swine of the disclosure is effective in preventing diseases (such as hog cholera), convenient in use, no toxicity, side effects or medical residue, which benefits human health.

The above description is merely preferred exemplary embodiments to explain the principles and implementations of the disclosure. For those skilled persons in the art, various modifications and variations can be made according to the concept of the disclosure. It is intended to cover various modifications and similar arrangements included within the spirit and scope of the appended claims which are to be accorded with the broadest interpretation so as to encompass all such modifications.

What is claimed is:

1. A feed additive for preventing hog cholera, wherein the feed additive for preventing hog cholera consists of following ingredients measured by weight: 20-50 sour jujubes, 10-18 radix bupleuri, 6-20 *codonopsis pilosula,* 10-20 honeysuckles, 10-20 *isatis* roots, 3-6 *astragalus propinquus,* 10-20 *myrica rubra* and 30-60 cactuses.

2. The feed additive for preventing hog cholera according to claim 1, wherein the feed additive for preventing hog cholera consists of 35 sour jujubes, 16 radix bupleuri, 12 *codonopsis pilosula,* 15 honeysuckles, 15 *isatis* roots, 5 *astragalus propinquus,* 15 *myrica rubra* and 50 cactuses.

3. A feed composition for preventing hog cholera, comprising a main feed and an additive, wherein the additive is processed by mixing, grinding, sifting and is mixed with the main feed, the additive consists of following ingredients measured by weight: 20-50 sour jujubes, 10-18 radix bupleuri, 6-20 *codonopsis pilosula,* 10-20 honeysuckles, 10-20 *isatis* roots, 3-6 *astragalus propinquus,* 10-20 *myrica rubra* and 30-60 cactuses.

4. The feed composition for preventing hog cholera according to claim 3, wherein the main feed comprises at least one of an animal protein product, marine product, milk product, grain product, plant protein product and processed grain by-product.

5. The feed composition for preventing hog cholera according to claim 3, wherein a ratio of the main feed to the additive is 500:3.

\* \* \* \* \*